United States Patent
Suppes

(10) Patent No.: US 12,292,394 B2
(45) Date of Patent: May 6, 2025

(54) APPARATUS AND METHOD FOR COMPUTED TOMOGRAPHY SYSTEM CALIBRATION

(71) Applicant: Baker Hughes Holdings LLC, Houston, TX (US)

(72) Inventor: Alexander Suppes, Garbsen (DE)

(73) Assignee: Baker Hughes Holdings LLC, Houston, TX (US)

( * ) Notice: Subject to any disclaimer, the term of this patent is extended or adjusted under 35 U.S.C. 154(b) by 275 days.

(21) Appl. No.: 18/107,067

(22) Filed: Feb. 8, 2023

(65) Prior Publication Data

US 2024/0264096 A1    Aug. 8, 2024

(51) Int. Cl.
*G01N 23/046*    (2018.01)
*H01M 50/105*    (2021.01)

(52) U.S. Cl.
CPC ........ *G01N 23/046* (2013.01); *H01M 50/105* (2021.01); *G01N 2223/303* (2013.01); *G01N 2223/304* (2013.01); *G01N 2223/611* (2013.01)

(58) Field of Classification Search
CPC ........... G01N 23/046; G01N 2223/303; G01N 2223/304; G01N 2223/611; G01N 33/0003; G01N 2223/33; G01N 2223/419; H01M 50/105; H01M 10/4285; Y02E 60/10; Y02P 70/50
See application file for complete search history.

(56) References Cited

U.S. PATENT DOCUMENTS

2021/0225032 A1*  7/2021  Hain ................. G06T 7/73

FOREIGN PATENT DOCUMENTS

CN    117704968 A  *  3/2024  ............. G06T 7/80

* cited by examiner

*Primary Examiner* — Edwin C Gunberg
*Assistant Examiner* — Richard O Toohey
(74) *Attorney, Agent, or Firm* — Mintz, Levin, Cohn, Ferris, Glovsky and Popeo, P.C.

(57) ABSTRACT

A system and method for calibrating a computed tomography (CT) scanner including scanning a calibration apparatus with the CT scanner, and determining a first scan edge of a first calibration layer, a second scan edge of a second calibration layer, and a floating point of an opening from the scan. The method also includes determining a first scan dimension and second scan dimension measured in the longitudinal direction from the first scan edge to the floating point, and the second scan edge to the floating point, respectively. The method also includes determining a first scan overhang based on a difference between the first scan dimension and the second scan dimension and comparing the first scan overhang to the calibration overhang. The method also includes determining a first level of uncertainty for the CT scanner based on the comparing.

20 Claims, 11 Drawing Sheets

APPARATUS AND METHOD FOR COMPUTED TOMOGRAPHY SYSTEM CALIBRATION

BACKGROUND

The present disclosure relates to an apparatus, system and method for computed tomography (CT) system calibration. Specifically, the present subject matter pertains to the calibration of CT systems used in measuring manufactured objects, such as lithium-ion (li-ion) batteries and other electronic devices.

In a battery, specifically, a lithium-ion battery, layers of cathodes and anodes can be stacked and/or rolled to produce stacked pouch cells and cylindrical or prismatic cells, respectively. Cathodes can often include a thin layer of aluminum to act as a current collector with a lithium-based compound applied to the surface of the aluminum in the form of a thin film. Cathodes in lithium-ion batteries can be made from a variety of materials, including lithium cobalt oxide ($LiCoO_2$), lithium manganese oxide ($LiMn_2O_4$), lithium iron phosphate ($LiFePO_4$), and lithium nickel cobalt aluminum oxide ($LiNiCoAlO_2$). Alternatively, anodes can often include a thin layer of copper to act as a current collector with a carbon-based material (i.e. graphite) applied to the surface of the aluminum.

Typically, the tips of anodes of the battery extend further than the tips of the anodes of the battery, producing what is called "overhang" or "OH". Determining OH measurements in a battery can be important, as they can affect the performance and reliability of the battery.

SUMMARY

An apparatus, system and method for calibrating a computed tomography (CT) scanner is provided. In one embodiment, the apparatus for calibrating a computed tomography (CT) scanner can include a plurality of body layers arranged to extend in a longitudinal direction of the apparatus. The apparatus can apparatus can also include at least one calibration pair configured to extend in the longitudinal direction of the apparatus and form an interleaved arrangement with the plurality of body layers. The calibration pair can include a first calibration layer having a first edge, a second calibration layer having a second edge, and an opening extending through the first calibration layer and the second calibration layer. The calibration pair can further include a first calibration dimension measured in the longitudinal direction from the first edge to a predetermined point within the opening, and a second calibration dimension measured in the longitudinal direction from the second edge to a predetermined point within the opening.

In another embodiment, the apparatus can further include a calibration overhang dimension measured as a difference between the first calibration dimension and the second calibration dimension. In another embodiment, the first calibration layer of the calibration pair is an anode layer made from a first material. In this embodiment, the second calibration layer of the calibration pair is a cathode layer made from a second material. In this embodiment, the plurality of body layers further include a body anode layer made from the first material and a body cathode layer made from the second material. The body anode layer and the body cathode layer can form an interleaved arrangement, and the plurality of body layers, the anode layer and the cathode layer are laminated within a battery housing to form a stacked pouch cell.

In another embodiment, the first calibration layer of the calibration pair is an anode layer made from a first material, and second calibration layer of the calibration pair is a cathode layer made from a second material. In this embodiment, the anode layer and the cathode layer are arranged in concentric layers in the longitudinal direction within a battery housing to form a cylindrical cell or a prismatic cell.

In another embodiment, the opening is circular, triangular, square, rectangular, pentagonal, or hexagonal in shape.

In another embodiment, the at least one calibration pair further includes a first calibration layer support structure having a first end and a second end. The first calibration layer support structure coupled to the first edge of the first calibration layer at the first end and coupled to the second end via at least one clamping mechanism. The at least one calibration pair can also include a second calibration layer support structure coupled to the second edge of the second calibration layer at the first end and coupled to the second end via the at least one clamping mechanism. The at least one clamping mechanism can be coupled to the second end of the first calibration layer support structure and the second end of the second calibration layer support structure to prevent bending of the at least one calibration pair.

In another embodiment, the first calibration layer support structure is formed integrally with the first calibration layer, and the second calibration layer support structure is formed integrally with the second calibration layer.

In another aspect a method for calibrating a computed tomography (CT) scanner is provided. In one embodiment the method can include scanning, by a CT scanner, an apparatus. The apparatus can include a plurality of body layers configured to extend in a longitudinal direction of the apparatus, at least one calibration pair configured to extend in the longitudinal direction of the apparatus and form an interleaved arrangement with the plurality of body layers. The at least one calibration pair including a first calibration layer having a first edge, a second calibration layer having a second edge, an opening extending through the first calibration layer and the second calibration layer. The apparatus can further include a first calibration dimension measured in the longitudinal direction from the first edge to a first predetermined point within the opening. The apparatus can further include a second calibration dimension measured in the longitudinal direction from the second edge to a second predetermined point within the opening. The apparatus can further include a calibration overhang measured as a difference between the first calibration dimension and the second calibration dimension. The method can further include determining, by at least one processor of a computing system, a first scan edge of the first calibration layer, a second scan edge of the second calibration layer, and a floating point within opening from the scan. The method can further include determining, by the at least one processor, a first scan dimension measured in the longitudinal direction from the first scan edge to the floating point. The method can further include determining, by the at least one processor, a second scan dimension measured in the longitudinal direction from the second scan edge to the floating point. The method can further include determining, by the at least one processor, a first scan overhang based on a difference between the first scan dimension and the second scan dimension. The method can further include comparing, by the at least one processor, the first scan overhang to the calibration overhang, determining, by the at least one processor, a first level of uncertainty for the CT scanner based on the comparing.

In another embodiment, the method can further include determining, by the at least one processor, a third scan dimension by iterating upon the first scan dimension based on the first level of uncertainty. In this embodiment, the method can further include determining, by the at least one processor, a fourth scan dimension by iterating upon the second scan dimension based on the first level of uncertainty. The method can further include determining, by the at least one processor, a second scan overhang based on a difference between the third scan dimension and the fourth scan dimension. The method can further include comparing, by the at least one processor, the second scan overhang to the calibration overhang, and determining, by the at least one processor, a second level of uncertainty for the CT scanner.

In another embodiment, the at least one calibration pair includes a plurality of calibration pairs and the first level of uncertainty includes a first scan dimension uncertainty vector dx1 calculated as a difference between the plurality of first scan dimensions and the plurality of first calibration dimensions. The at least one calibration pair also includes a second scan dimension uncertainty vector dx2 calculated as a difference between the plurality of second scan dimensions and the plurality of second calibration dimensions.

In another embodiment, the first calibration layer of the calibration pair is an anode layer made from a first material, and second calibration layer of the calibration pair is a cathode layer made from a second material. In this embodiment, the plurality of body layers further include a body anode layer made from the first material, and a body cathode layer made from the second material. The body anode layer and the body cathode layer form an interleaved arrangement, and the plurality of body layers, the anode layer and the cathode layer are laminated within a battery housing to form a stacked pouch cell.

In another embodiment, the first calibration layer of the calibration pair is an anode layer made from a first material, and second calibration layer of the calibration pair is a cathode layer made from a second material. The anode layer and the cathode layer are arranged in concentric layers in the longitudinal direction within a battery housing to form a cylindrical cell or a prismatic cell.

In another aspect a system for calibrating a computed tomography (CT) scanner is provided. In one embodiment, the system includes an apparatus, such as the apparatus discussed above. The system also includes a computing system communicatively coupled to a CT scanner, including at least one processor. The processor can be arranged to scan the apparatus, and determine a first scan edge of the first calibration layer, a second scan edge of the second calibration layer, and a floating point within the opening. The processor can also be arranged to determine a first scan dimension measured in the longitudinal direction from the first scan edge to the floating point. The processor can also be arranged to determine a second scan dimension measured in the longitudinal direction from the second scan edge to the floating point, and determine a first scan overhang based on a difference between the first scan dimension and the second scan dimension. The processor can also be arranged to compare the first scan overhang to the calibration overhang, and determine a first level of uncertainty for the CT scanner based on the comparing.

In another embodiment, the first level of uncertainty includes a first scan dimension uncertainty dx1 calculated as a difference between the first scan dimension and the first calibration dimension. The first level of uncertainty also includes a second scan dimension uncertainty dx2 calculated as a difference between the second scan dimension and the second calibration dimension.

In another embodiment, the system also includes a measuring device configured to measure the first calibration dimension, the second calibration dimension, the calibration edge offset, and/or the calibration alignment.

In another embodiment, the first calibration layer of the calibration pair is an anode layer made from a first material, and second calibration layer of the calibration pair is a cathode layer made from a second material. The plurality of body layers can include a body anode layer made from the first material. The plurality of body layers can also include a body cathode layer made from the second material. The body anode layer and the body cathode layer form an interleaved arrangement, and the plurality of body layers, the anode layer and the cathode layer are laminated within a battery housing to form a stacked pouch cell.

In another embodiment, the first calibration layer of the calibration pair is an anode layer made from a first material, and second calibration layer of the calibration pair is a cathode layer made from a second material. The anode layer and the cathode layer are rolled in the longitudinal direction and placed within a battery housing to form a cylindrical cell or a prismatic cell.

In another embodiment, the at least one calibration pair can further include a first calibration layer support structure arranged to couple at a first end to the first edge of the first calibration layer and configured to couple at a second end to at least one clamping mechanism. The at least one calibration pair can further include a second calibration layer support structure arranged to couple at a first end to the second edge of the second calibration layer and arranged to couple at a second end to the at least one clamping mechanism. The at least one clamping mechanism arranged to clamp the second end of the first calibration layer support structure and the second end of the second calibration layer support structure to prevent bending of the at least one calibration pair.

In another embodiment, the first calibration layer support structure is formed integrally with the first calibration layer, and the second calibration layer support structure is formed integrally with the second calibration layer.

DESCRIPTION OF DRAWINGS

These and other features will be more readily understood from the following detailed description taken in conjunction with the accompanying drawings, in which.

It is noted that the drawings are not necessarily to scale. The drawings are intended to depict only typical aspects of the subject matter disclosed herein, and therefore should not be considered as limiting the scope of the disclosure.

DETAILED DESCRIPTION

Traditionally, there has been no way to accurately validate the overhang (OH) measurements in lithium ion batteries as calculated by CT scanners. OH is an important quality metric that is calculated as the distance between a tip of an anode and a tip of a cathode in a lithium ion battery. OH is incorporated in batteries to ensure that an anode is opposite of a cathode even in the case where the anode and cathode are slightly misaligned during manufacturing (e.g. in cell winding or electrode stacking). OH is strictly monitored by manufacturers. Without useful systems and methods for calibrating and/or validating the scans provided by CT scanners, however, it can be difficult to detect OH in batteries which can lead to over compensations in manufacturing which can adversely increase scrap.

The systems and methods described herein addresses the aforementioned shortcomings. For example, one or more embodiments of the system herein can include a phantom apparatus for calibrating a CT system to ensure accurate scanning of lithium-ion batteries or other electronic devices and accurate determination of OH. The phantom apparatus can include a plurality of body layers and at least one calibration pair configured to form an interleaved arrangement with the plurality of body layers. The calibration pair can include a first calibration layer having a first edge and a first opening, and a second calibration layer having a second edge and a second opening extending through the second calibration layer. A measuring device can be used to accurately calculate an overhang between the first calibration layer and the second calibration layer which can then be used to compare to an overhang determined by a CT system in order to calibrate the CT system. It should be noted that it can be desirable to determine the OH for all edges of a battery.

The apparatuses, systems and methods described herein include, by way of non-limiting example, can provide technical solutions to technical problems such as calibrating a CT scanner to ensure that the measurements obtained from images taken by the scanner are accurate and of high quality. Such accuracy and high quality are essential for accurately measuring OH in li-ion batteries and other electronic devices. While many of the examples provided herein are in regard to li-ion batteries, it is important to note that the apparatuses, systems and methods described herein are capable of calibrating CT systems for a variety of applications including other battery applications, layered composite applications and or the like.

Figure 1:
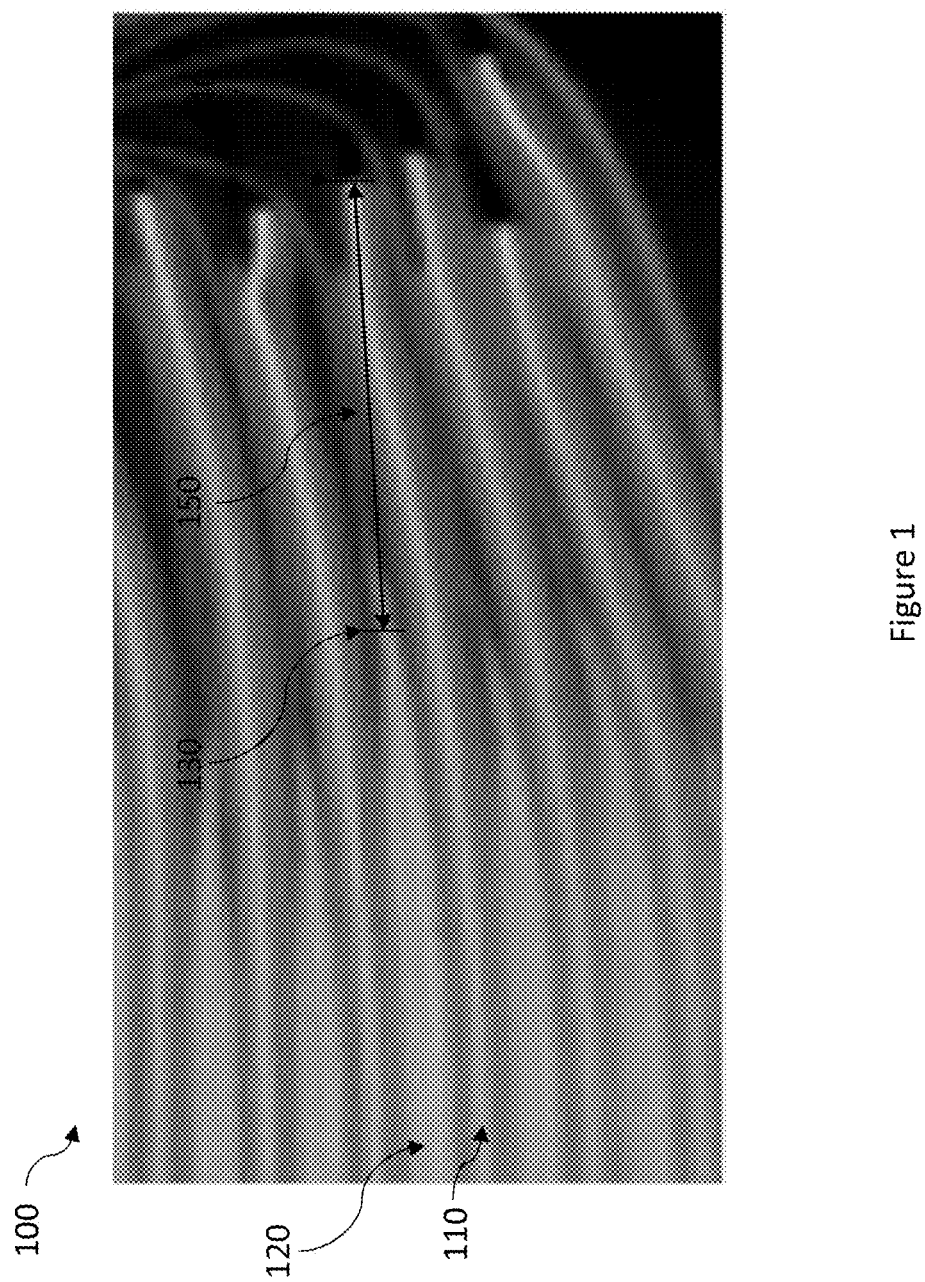
FIG. 1 illustrates an example of a CT scan taken by a CT scanner showing a plurality of cathodes and a plurality of anodes of a li-ion battery.

FIG. 1 is an example of a CT scan 100 taken by a CT scanner 160 (not shown) showing a plurality of anodes 110 and a plurality of cathodes 120 of a li-ion battery. Anodes are typically made of a lithium-based compound and coated in copper, while cathodes are typically made of a carbon-based material, such as graphite or other material and coated in aluminum. The overhang (OH) in the battery can be calculated as the distance 150 between the tip 140 of an anode 110 and the tip 130 of a cathode 120. This measurement can vary dramatically throughout a battery and the measurements derived by a CT system can often be inaccurate as a result of the imaging and image processing capabilities of the specific system (e.g. tip detection capabilities).

Figure 2:
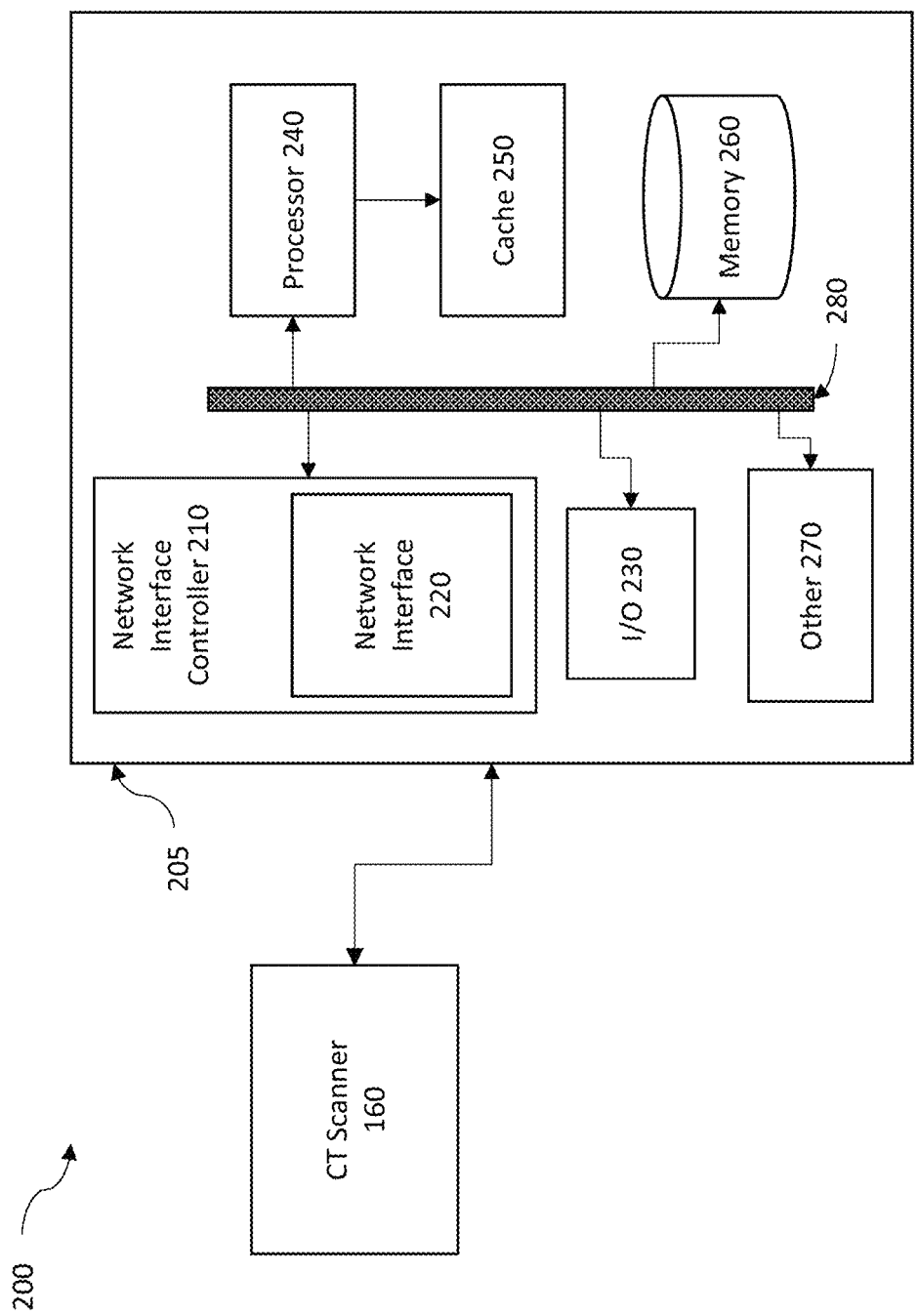
FIG. 2 is a block diagram of an example architecture of a CT system, including a computing system configured to receive data from a CT scanner according to some implementations of the current subject matter.

FIG. 2 is a block diagram of an example architecture of a CT system 200, including a computing system 205 configured to receive data from a CT scanner 160. In broad overview, the computing system 205 can include at least one processor 240 for performing actions in accordance with instructions, and one or more memory devices 250 and/or 260 for storing instructions and data. The illustrated example computing system 205 includes one or more processors 240 in communication, via a bus 280, with memory 260 and with at least one network interface controller 210 with a network interface 220 for connecting to the CT scanner 160. The one or more processors 240 are also in communication, via the bus 280, with each other and with the CT scanner 160, and any other devices 270. The processor 240 illustrated incorporates, or is directly connected to, cache memory 250. Generally, a processor will execute instructions received from memory. In some embodiments, the computing system 205 can be configured within a cloud computing environment, a virtual or containerized computing environment, and/or a web-based micro services environment or physically incorporated within the housing of CT scanner.

In more detail, the processor 240 can be any logic circuitry that processes instructions, e.g., instructions fetched from the memory 260 or cache 250. In many embodiments, the processor 240 is an embedded processor, a microprocessor unit or special purpose processor. The computing system 205 can be based on any processor, e.g., suitable digital signal processor (DSP), or set of processors, capable of operating as described herein. In some embodiments, the processor 240 can be a single core or multi-core processor. In some embodiments, the processor 240 can be composed of multiple processors.

The memory 260 can be any device suitable for storing computer readable data. The memory 260 can be a device with fixed storage or a device for reading removable storage media. Examples include all forms of non-volatile memory, media and memory devices, semiconductor memory devices (e.g., EPROM, EEPROM, SDRAM, flash memory devices, and all types of solid state memory), magnetic disks, and magneto optical disks. A computing device 205 can have any number of memory devices 260.

The cache memory 250 is generally a form of high-speed computer memory placed in close proximity to the processor 240 for fast read/write times. In some implementations, the cache memory 250 is part of, or on the same chip as, the processor 240.

The network interface controller 210 manages data exchanges via the network interface 220. The network interface controller 210 handles the physical, media access control, and data link layers of the Open Systems Interconnect (OSI) model for network communication. In some implementations, some of the network interface controller's tasks are handled by the processor 240. In some implementations, the network interface controller 210 is part of the processor 240. In some implementations, a computing device 205 has multiple network interface controllers 210. In some implementations, the network interface 220 is a connection point for a physical network link, e.g., an RJ 45 connector. In some implementations, the network interface controller 210 supports wireless network connections via network interface port 220. Generally, a computing device 205 exchanges data with the CT scanner 160, via physical or wireless links to a network interface 220. In some implementations, the network interface controller 210 implements a network protocol such as LTE, TCP/IP Ethernet, IEEE 802.11, IEEE 802.16, or the like.

The CT scanner 160 can be connected to the computing device 205 via a network interface port 220. The other devices 270 can include an I/O interface 230, external serial device ports, and any additional co-processors. For example, a computing system 205 can include an interface (e.g., a universal serial bus (USB) interface, or the like) for connecting input devices (e.g., a keyboard, microphone, mouse, or other pointing device), output devices (e.g., video display, speaker, refreshable Braille terminal, or printer), or additional memory devices (e.g., portable flash drive or external media drive). In some implementations an I/O device is incorporated into the computing system 205, e.g., a touch screen on a tablet device. In some implementations, a computing device 205 includes an additional device 270 such as a co-processor, e.g., a math co-processor that can assist the processor 240 with high precision or complex calculations.

Figure 3:
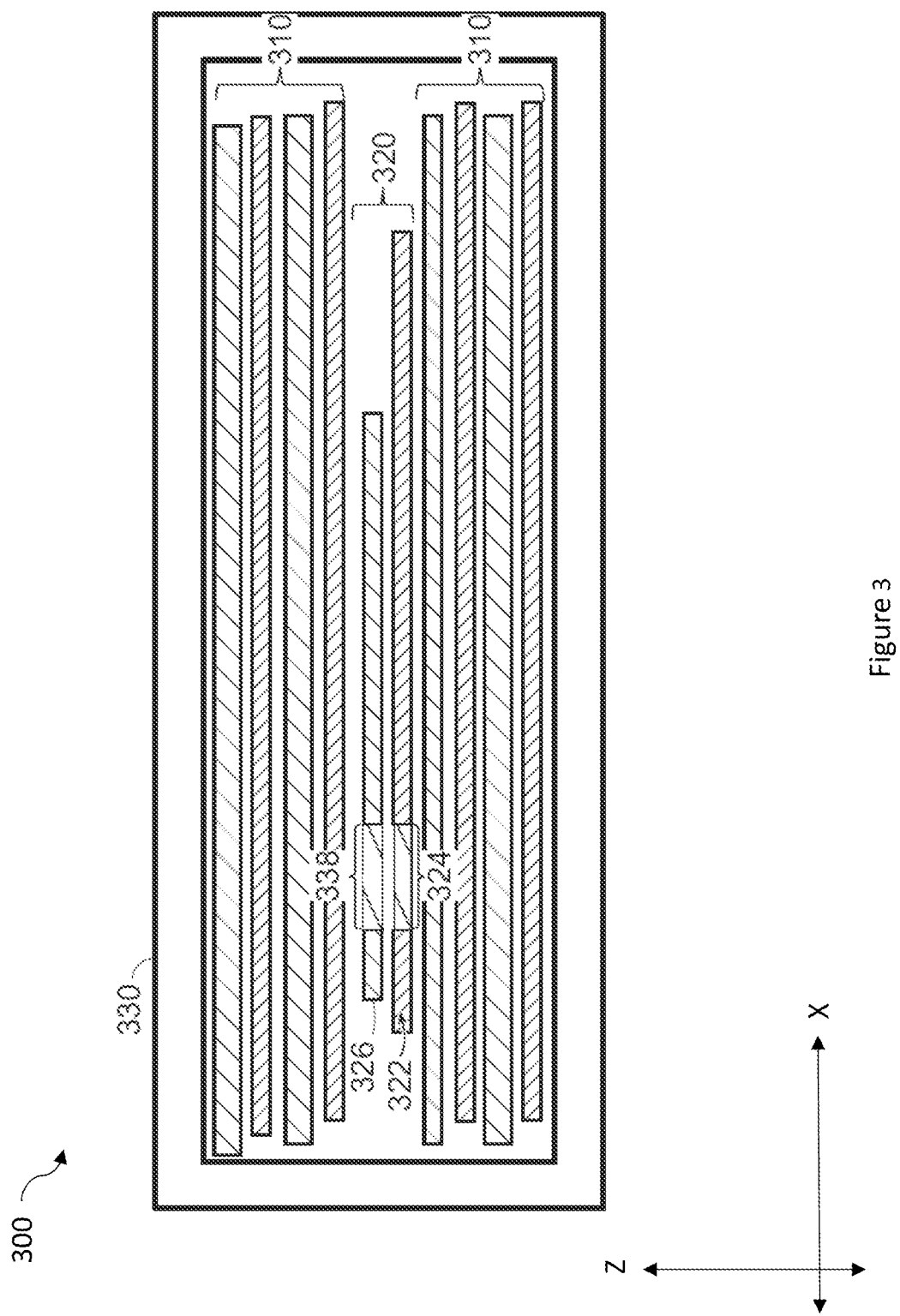
FIG. 3 is a diagram illustrating an example of a phantom apparatus according to some implementations of the current subject matter.

FIG. 3 is a diagram illustrating an example of a phantom apparatus 300 according to an embodiment described herein. In some embodiments, the apparatus 300 can include a plurality of body layers 310 configured to extend in a longitudinal direction of the apparatus 300 along axis X. In some embodiments, the plurality of body layers 310 can be made from stacked layers of cathodes and anodes to resemble a li-ion battery. In this embodiment, the plurality of body layers 310 can be made from copper with a lithium-based compound applied to the surface to resemble an anode, and/or aluminum with a carbon-based material (e.g. graphite) applied to the surface to resemble a cathode. In other embodiments, the plurality of body layers 310 can be a plurality of composite carbon layers, or the like. In some embodiments, the plurality of body layers and the at least one calibration pair can be place within a housing 330. In other embodiments, one or more of the plurality of body layers 310 can be rolled about an axis perpendicular to the X and Z axes (e.g. a Y axis coming out of the page), for example, and placed within a housing 330 to form a cylindrical cell or a prismatic cell. In some embodiments, the plurality of body layers 310 can further include an electrolyte layer. In some embodiments, the electrolyte can be made of a mixture of lithium salts in an organic solvent. In some embodiments, the plurality of body layers can further include additional layers, such as a separator layer and/or a protective layer.

The apparatus 300 can further include at least one calibration pair 320 configured to extend in the longitudinal direction of the apparatus 300 and form an interleaved arrangement with the plurality of body layers 310. In some embodiments, the at least one calibration pair 320 can include a first calibration layer 322 and a second calibration layer 326 (described in further detail below in FIGS. 4-7). In some embodiments, the first calibration layer 322 can be made from copper with a lithium-based compound applied to the surface to resemble an anode. In some embodiments, the second calibration layer 326 can be made from aluminum with a carbon-based material (i.e. graphite) applied to the surface to resemble a catode. In other embodiments, the at least one calibration pair 320 can be a pair of composite carbon layers, or the like.

When scanning an object with a CT scanner, the quality of the image can vary depending on the scanner. Accordingly, edges of objects being scanned can appear blurry and it can be hard for a computing system coupled to the scanner to detect edges of objects. However, it can be easier for the computing system coupled to the scanner to accurately determine a middle point between two or more blurred edges. Accordingly, the first calibration layer 322 and the second calibration layer 328 can include a first opening 324 and a second opening 328 respectively.

Figure 4:
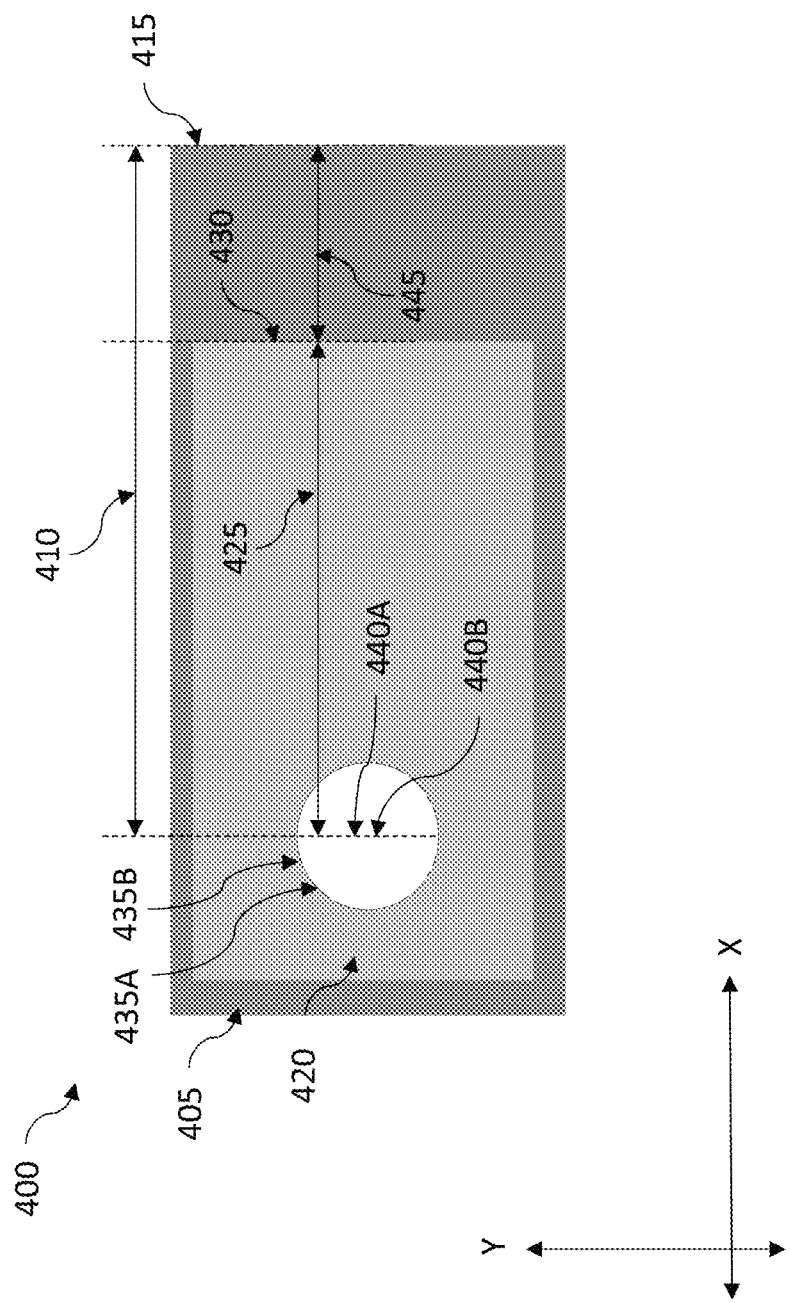
FIG. 4 is a diagram illustrating an example of a top view of a calibration pair according to some implementations of the current subject matter.

FIG. 4 is a diagram illustrating an example of a top view 400 of a calibration pair according to an embodiment described herein. In some embodiments, the calibration pair seen in 400 can include a first calibration layer 405 and a second calibration layer 420. The first calibration layer 405 can include a first edge 415, a first opening 435A extending through the first calibration layer 405, and a second calibration layer 420 having a second edge 430, and a second opening 435B extending through the second calibration layer 420. In some embodiments the first opening 435A can be circular, triangular, square, rectangular, pentagonal, or hexagonal in shape. In some embodiments the second opening 435B can be circular, triangular, square, rectangular, pentagonal, or hexagonal in shape. In some embodiments, the first opening 435A can be configured to align with the second opening 435B. In some embodiments, due to manufacturing tolerances, however, some amount of offset may exist between the first opening 435A and the second opening 435B.

In some embodiments, a first calibration dimension 410 can be measured in the longitudinal direction, as the perpendicular distance from the first edge 415 to a first predetermined point 440A of the first opening 435A. In some embodiments, the predetermined point 440A can be the center of the first opening 435A. In other embodiments, the predetermined point 440A can be another advantageously placed point in the first opening 435A. In some embodiments, a second calibration dimension 425 can be measured in the longitudinal direction, as the perpendicular distance from the second edge 430 to a second predetermined point 440B of the second opening 435B. In some embodiments, the second predetermined point 440B can be the center of the second opening 435B. In other embodiments, the second predetermined point 440B can be another advantageously placed point in the second opening 435B. In some embodiments, the first predetermined point 440A and the second predetermined point 440B can be coincident. A calibration overhang 445 can be measured as a difference between the first calibration dimension 410 and the second calibration dimension 425. In some embodiments the above measurements can additionally be made for all of the edges of the calibration pair seen in 400. In some embodiments, the first calibration dimension 410, the second calibration dimension 425 and the calibration overhang 445 can be determined using an external measurement device to ensure accuracy. In some embodiments, the external measurement device can be an optical or tactile measurement device or the like.

Figure 5:
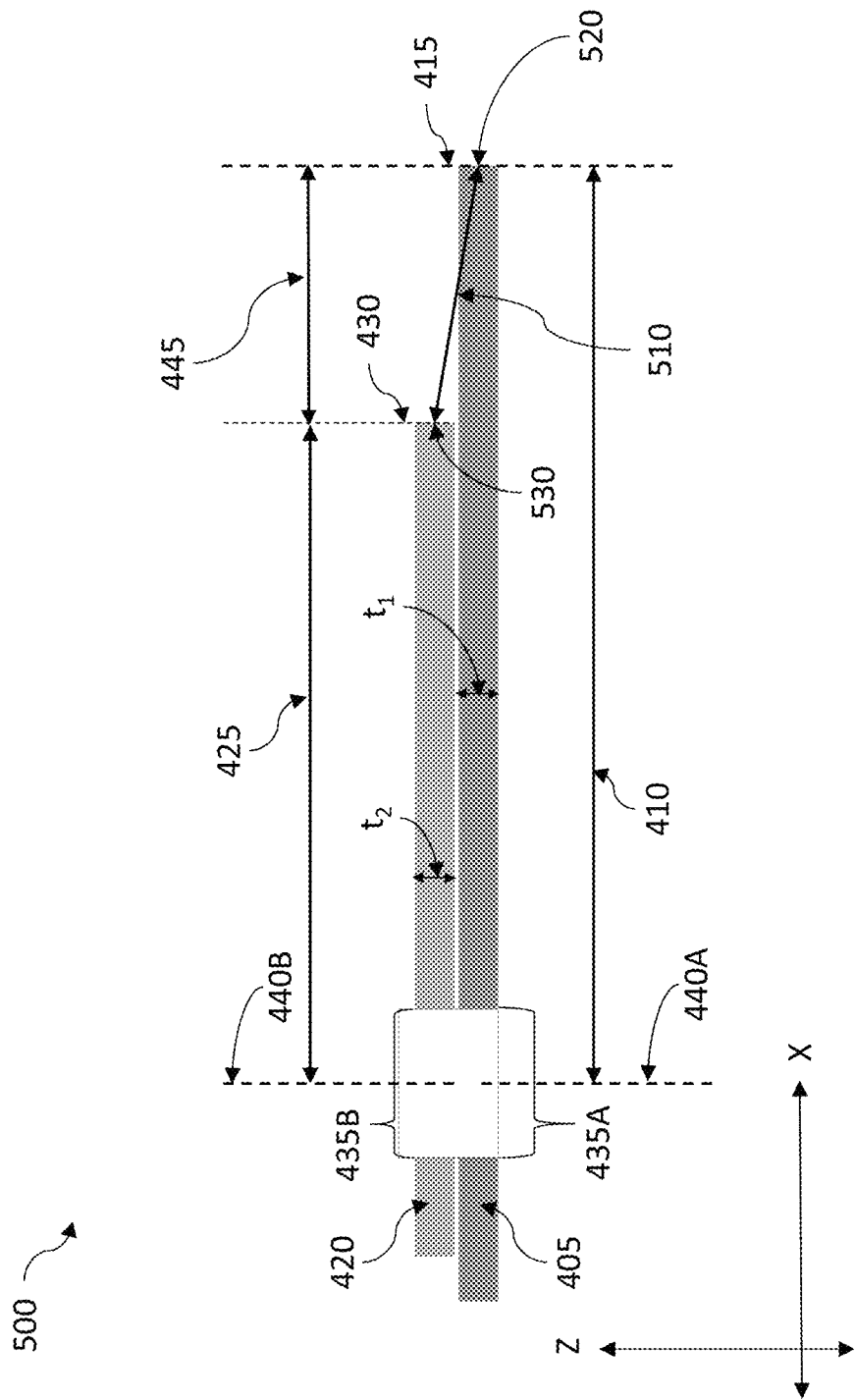
FIG. 5 is a diagram illustrating an example of a side view of the calibration pair of FIG. 4.

FIG. 5 is a diagram illustrating an example of a side view 500 of the calibration pair described above in relation to FIG. 4. In some embodiments, a thickness $t_1$ of the first calibration layer 405 and a thickness $t_2$ of the second calibration layer 420 can be negligible. In this case, the calibration overhang 445 can be measured simply as the difference between the first calibration dimension 410 and the second calibration dimension 425. In other embodiments, the thickness $t_1$ of the first calibration layer 405 and the thickness $t_2$ of the second calibration layer 420 can be significant. In this case, the calibration overhang 445 can be measured simply as the difference between the first calibration dimension 410 and the second calibration dimension 425. In other embodiments, the calibration overhang can be calculated as the diagonal distance 510 between a first middle point (tip) 520 of the first edge 415 and a second middle point (tip) 530 of the second edge 430, when viewing the apparatus from the X-Z plane. In the event the calibration pair has a small amount of curvature, the calibration overhang 445 can be measured along the curvature of the calibration pair. In some embodiments, the first calibration dimension 410, second calibration dimension 425, and calibration overhang 445 (or 510) can be calculated during manufacturing by an external measurement device (discussed in further detail below in reference to FIG. 8 and FIG. 10).

Figure 6A:
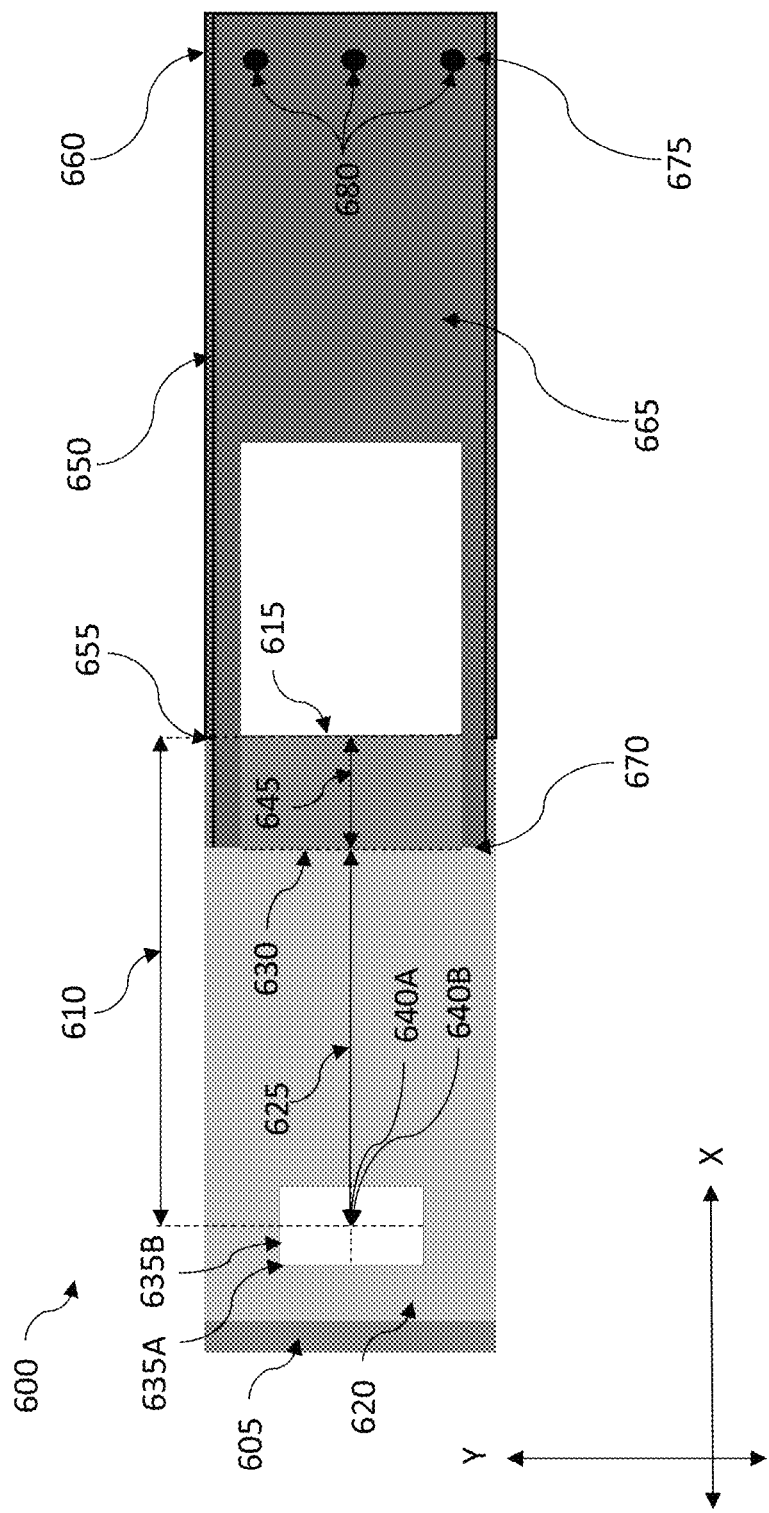
FIG. 6A is a diagram illustrating an example of a top view of another calibration pair according to some implementations of the current subject matter.

FIG. 6A is a diagram illustrating top view of another embodiment of a calibration pair 600. In some embodiments, the calibration pair 600 can include a first calibration layer 605 and a second calibration layer 620. The first calibration layer 605 can include a first edge 615, a first opening 635A extending through the first calibration layer 605, and a second calibration layer 620 having a second edge 630, and a second opening 635B extending through the second calibration layer 620. In some embodiments the first opening 635A can be circular, triangular, square, rectangular, pentagonal, or hexagonal in shape. In some embodiments the second opening 635B can be circular, triangular, square, rectangular, pentagonal, or hexagonal in shape. In some embodiments, the first opening 635A can be configured to align with the second opening 635B. In some embodiments, due to manufacturing tolerances, however, some amount of offset may exist between the first opening 635A and the second opening 635B.

In some embodiments, a first calibration dimension 610 can be measured in the longitudinal direction, as the perpendicular distance from the first edge 615 to a first predetermined point 640A of the first opening 635A. In some embodiments, the predetermined point 640A can be the center of the first opening 635A. In other embodiments, the predetermined point 640A can be another advantageously placed point in the first opening 635A. In some embodiments, a second calibration dimension 625 can be measured in the longitudinal direction, as the perpendicular distance from the second edge 630 to a second predetermined point 640B of the second opening 635B. In some embodiments, the second predetermined point 640B can be the center of the second opening 635B. In other embodiments, the second predetermined point 640B can be another advantageously placed point in the second opening 635B. In some embodiments, the first predetermined point 640A and the second predetermined point 640B can be coincident. A calibration overhang 645 can be measured as a difference between the first calibration dimension 610 and the second calibration dimension 625. In some embodiments the above measurements can additionally be made for all of the edges of the calibration pair 600. In some embodiments, the first calibration dimension 610, the second calibration dimension 625 and the calibration overhang 645 can be determined using an external measurement device to ensure accuracy.

In some embodiments, the calibration pair 600 can further include a first calibration layer support structure 650 having a first end 655 and a second end 660. In some embodiments, the first calibration layer support structure 650 can be configured to mitigate bending of the first calibration layer 605. In some embodiments, the first calibration layer support structure 650 can be coupled to the first edge 615 of the first calibration layer 605 at the first end 655 and to an attachment mechanism 680 at the second end 660. In some embodiments, the attachment mechanism 680 can be configured to minimize bending of the calibration pair. In some embodiments, the first calibration layer support structure 650 can be formed integrally with the first calibration layer 605. In some embodiments, the first calibration layer support structure 650 can be made from the same material as the first calibration layer 605, or from a different material.

In some embodiments, the calibration pair 600 can further include a second calibration layer support structure 665 having a first end 670 and a second end 675. In some embodiments, the second calibration layer support structure 665 can be configured to mitigate bending of the second calibration layer 620. In some embodiments, the second calibration layer support structure 665 can be coupled to the first edge 630 of the second calibration layer 620 at the first end 670 and to the attachment mechanism 680 at the second end 675. In some embodiments, the second calibration layer support structure 665 can be formed integrally with the second calibration layer 620. In some embodiments, the second calibration layer support structure 665 can be made from the same material as the second calibration layer 620, or from a different material. In some embodiments, the first calibration layer support structure 650 and the second calibration layer support structure 665 can be formed integrally as a singular support structure.

Figure 6B:
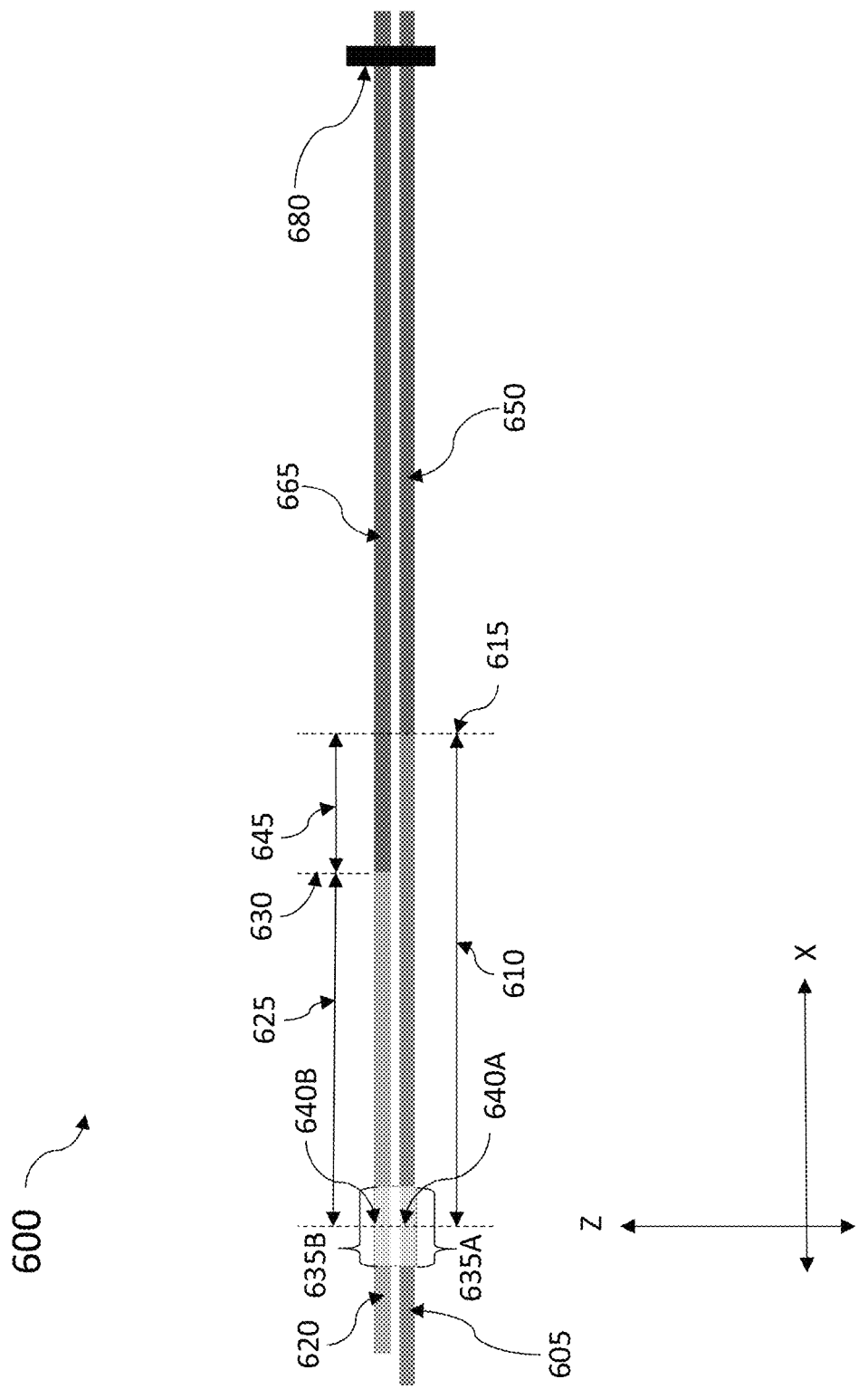
FIG. 6B is a diagram illustrating an example of a side view of the calibration pair of FIG. 6A.

FIG. 6B is a diagram illustrating an example of a side view of the calibration pair 600 described above in relation to FIG. 6A.

Figure 7:
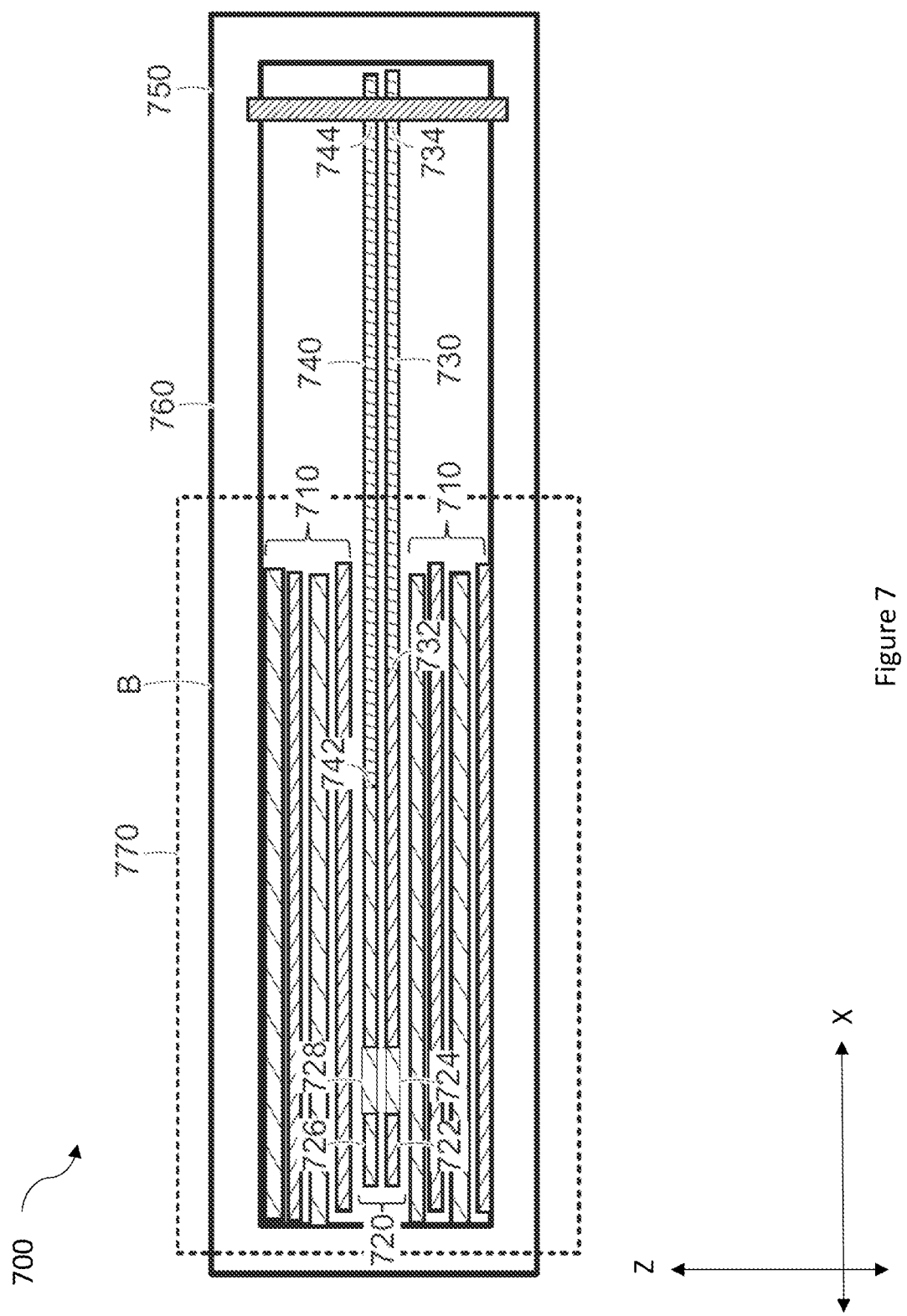
FIG. 7 is a diagram illustrating an example of another phantom apparatus according to some implementations of the current subject matter.

FIG. 7 is a diagram illustrating an example of another phantom apparatus 700 according to an embodiment described herein. In some embodiments, the apparatus 700 can include a plurality of body layers 710 configured to stack along the axis Z and extend in a longitudinal direction of the apparatus 700 along axis X. In some embodiments, the plurality of body layers 710 can be made from stacked layers of cathodes and anodes to resemble a li-ion battery. In this embodiment, the plurality of body layers 710 can be made from copper with a lithium-based compound applied to the surface to resemble an anode, and/or aluminum with a carbon-based material (i.e. graphite) applied to the surface to resemble a cathode. In other embodiments, the plurality of body layers 710 can be a plurality of composite carbon layers, or the like. In some embodiments, the plurality of body layers and the at least one calibration pair can be place within a housing 760. In other embodiments, one or more of the plurality of body layers 710 can be rolled about an axis perpendicular to the X and Z axes (e.g. a Y axis coming out of the page), for example, and placed within a housing 760 to form a cylindrical cell or a prismatic cell. In some embodiments, the plurality of body layers 710 can further include an electrolyte layer. In some embodiments, the electrolyte can be made of a mixture of lithium salts in an organic solvent. In some embodiments, the plurality of body layers can further include additional layers, such as a separator layer and/or a protective layer.

The apparatus 700 can further include at least one calibration pair 720 configured to extend in the longitudinal direction of the apparatus 700 and form an interleaved arrangement with the plurality of body layers 710. In some embodiments, the at least one calibration pair 720 can include a first calibration layer 722 having a first opening 724 and a second calibration layer 726 having a second opening 728. In some embodiments, the first calibration layer 722 can be made from copper with a lithium-based compound applied to the surface to resemble an anode. In some embodiments, the second calibration layer 722 can be made from aluminum with a carbon-based material (i.e. graphite) applied to the surface to resemble a cathode. In other embodiments, the at least one calibration pair 720 can be a pair of composite carbon layers, or the like.

In some embodiments, the apparatus 700 can further include a first calibration layer support structure 730 configured to mitigate bending of the first calibration layer 722 during measuring of the first calibration layer 722 by an external measuring device and/or during scanning of the apparatus by a CT scanner. In some embodiments, the first calibration layer support structure 730 can be coupled at a first end 732 to the first calibration layer 722 and at a second end 734 to a clamping mechanism 750. In some embodiments, the clamping mechanism 750 can be integral with the housing 760 of the apparatus 700. In other embodiments, the clamping mechanism 750 can be provided separately from the apparatus 700. In some embodiments, the first calibration layer support structure 730 can be formed integrally with the first calibration layer 722. In some embodiments, the first calibration layer support structure 730 can be made from the same material as the first calibration layer 722, or from a different material.

In some embodiments, the apparatus 700 can further include a second calibration layer support structure 740 configured to mitigate bending of the second calibration layer 726 during measuring of the second calibration layer 726 by an external measuring device and/or during scanning of the apparatus by a CT scanner. In some embodiments, the second calibration layer support structure 740 can be coupled at a first end 742 to the second calibration layer 726 and at a second end 744 to the clamping mechanism 750. In some embodiments, the second calibration layer support structure 740 can be formed integrally with the second calibration layer 726. In some embodiments, the second calibration layer support structure 740 can be made from the same material as the second calibration layer 726, or from a different material. In some embodiments, the first calibration layer support structure 730 and the second calibration layer support structure 740 can be formed integrally as a singular support structure.

In some embodiments, a CT scanner being calibrated can be configured to only scan a portion of the apparatus 700, for example, portion 770.

Figure 8:
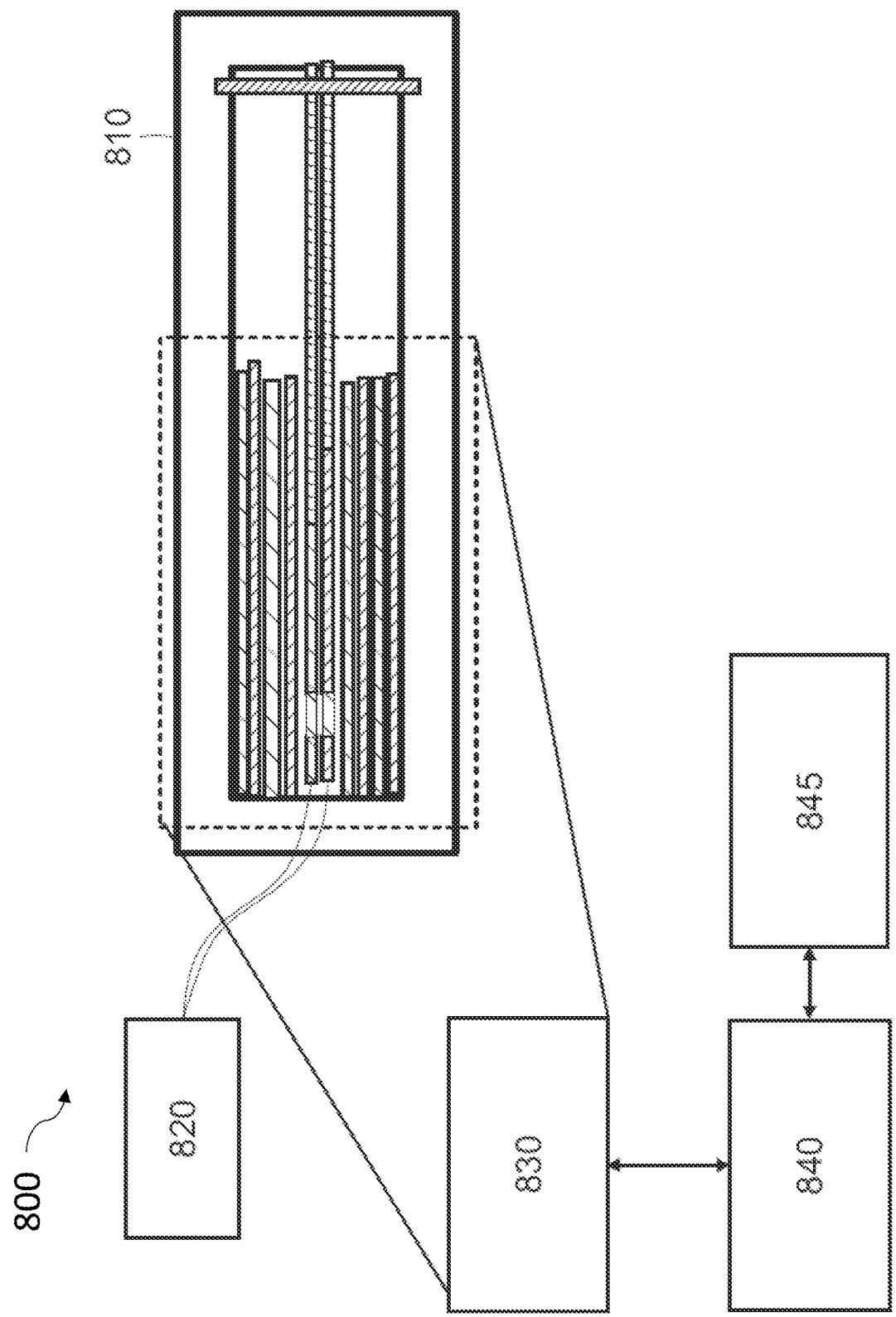
FIG. 8 is a diagram illustrating an example of a system according to some implementations of the current subject matter.

FIG. 8 is a diagram illustrating an example of a system 800 according to an embodiment described herein. In some embodiments, the system can include an apparatus 810. In some embodiments, the apparatus can be similar to the apparatuses described above in relation to FIGS. 3-9. In some embodiments, the system can further include the measuring device 820 configured to measure a first calibration dimension and a second calibration dimension. In some embodiments, the measuring device 820 can be configured to measure the first dimension and the second dimension with a very high level of accuracy so that it can be assumed that the first calibration dimension and the second calibration dimension are the "actual" dimensions of the apparatus. A calibration overhang can be derived from the first calibration dimension and the second calibration dimension using the methods discussed in reference to FIG. 5. In some embodiments, the measuring device 820 can be an optical or tactile measurement device or the like.

In some embodiments, the system can further include a CT scanner 830 that requires calibration. The CT scanner 830 can be configured to scan the apparatus 810 and provide the scan to a computing system 840 communicatively coupled to the CT scanner 830. In some embodiments, the computing system can be similar to the computing system 205, described above in relation to FIG. 2. In some embodiments, the computing system 840 can include a graphical user interface 845 configured to receive user inputs, and at least one processor configured to determine a level of uncertainty associated with the CT scanner 830. The process of determining the level of uncertainty is described in greater detail below in reference to FIG. 10.

Figure 9:
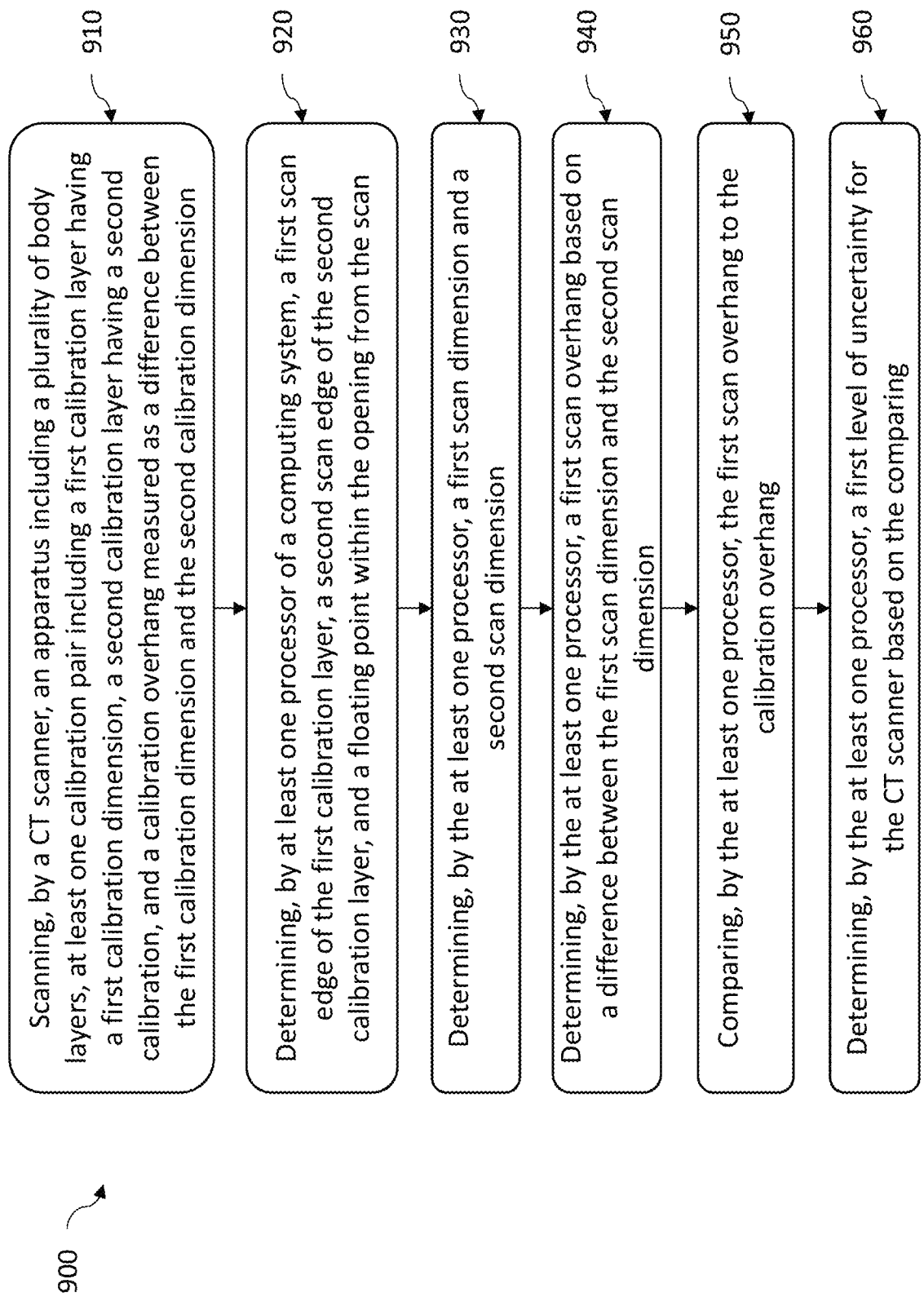
FIG. 9 is an example of a method for calibrating a CT scanner according to some implementations of the current subject matter.

FIG. 9 is an example of a method 900 for calibration of a CT scanner according to an embodiment described herein. The method 900 can include a step 910 of scanning, by a CT scanner, an apparatus (i.e. an apparatus similar to those discussed in FIGS. 3-7). The apparatus can include a plurality of body layers, at least one calibration pair including a first calibration layer having a first calibration dimension, a second calibration layer having a second calibration, and a calibration overhang measured as a difference between the first calibration dimension and the second calibration dimension.

The method 900 can include a step 920 of determining, by at least one processor of a computing system, a first scan edge of the first calibration layer, a second scan edge of the second calibration layer. In some embodiments, this determining can include detecting, by the at least one processor, the first calibration edge 415 and the second calibration edge 430. In some embodiments, the detecting can be done by selecting points along the first calibration edge 415 and the second calibration edge 430 edge. In some embodiments, the selecting of points can be done automatically by the at least one processor. In some embodiments, the selecting of points can be done by a user by interacting with a user interface display coupled to the computing device. In some embodiments, the at least one processor can be configured generate the first scan edge and the second scan edge by fitting a line to the first calibration edge 415 and the second calibration edge 430, respectively based on the points selected.

In some embodiments, the determining can include detecting a floating point within the opening from the scan. In some embodiments, the detecting of the floating point can be done by selecting points on the edge of the first opening and/or the second opening. In some embodiments, the selecting of points can be done automatically by the computing system. In some embodiments, the selecting of points can be done by a user by interacting with the user interface display coupled to the computing device. In some embodiments, the at least one processor can be configured to fit a shape to the opening based on the points selected to aid in the floating point selection. In some embodiments, the floating point, the first predetermined point, and the second predetermined point are the same point.

The method 900 can further include a step 930 of determining, by the at least one processor, a first scan dimension and a second scan dimension. In some embodiments, this determining can include defining a first axis, perpendicular to the first scan edge and configured to pass through the floating point. In some embodiments, this determining can include defining a second axis, perpendicular to the second scan edge and configured to run through the floating point. In some embodiments, the first axis and the second axis can be equivalent. In some embodiments, the first scan dimension can be measured as the distance between the first scan edge and the floating point, along the first axis. In some embodiments, the second scan dimension can be measured as the distance between the second scan edge and the floating point, along the first axis.

The method 900 can further include a step 940 of determining, by the at least one processor, a first scan overhang. In some embodiments, the thickness $t_1$ of the first calibration layer and the thickness $t_2$ of the second calibration layer are negligible when it comes to determining the first scan overhang. In this embodiment, the first scan overhang can be determined by simply determining, by the at least one processor, the difference between the first scan dimension and the second scan dimension.

In some embodiments, however, $t_1$ and $t_2$ are not negligible, and the first scan overhang can be determined by generating, by the at least one processor, a CT slice image from the volumetric data of the scan. In some embodiments, the CT slice image can be generated by resampling of the volumetric data in a plane parallel to the X-Z plane (in reference to FIGS. 3, 5, 6B, and 7. In some embodiments, the determining of the first scan overhang can further include determining a first scan middle point (tip) of the first scan edge and a second middle point (tip) of the second scan edge, when viewing the apparatus from the X-Z plane. In some embodiments, the first scan overhang can be a distance between the first scan middle point (tip) of the first scan edge and a second middle point (tip) of the second scan edge.

In other embodiments, the first calibration layer the second calibration layer can be curved. In this embodiment, the first scan overhang can be determined by measuring the distance between the first scan edge and the second scan edge along the curvature of the first and second calibration layers.

In some embodiments, the first scan edge and the second scan edge can be determined automatically by the at least one processor. In other embodiments, the computing system of the CT scanner can further include a graphical user interface configured to display the scanned image of the apparatus. In this embodiment, a user can identify the first scan edge and the second scan edge by selecting points on the scanned image via the graphical user interface.

In some embodiments, due to manufacturing capabilities, the calibration pair can have non-ideal alignments. For example, the first edge and/or the second edge can be non-orthogonal, the first edge and/or the second edge can be slightly non-straight, and/or the first calibration layer and the second calibration layer can be slightly shifted relative to one another or bent, causing the first opening and the second opening to not be perfectly aligned. Additionally, the first opening and the second opening can be slightly non-circular (or triangular, square, rectangular, pentagonal, or hexagonal, etc.). In these non-ideal embodiments, the computing system can be configured to determine the first scan edge, the second scan edge, the floating point, the first scan dimension, the second scan dimension, and the first scan overhang using the methods described above in reference steps 920-940 of method 900.

The method 900 can further include a step 950 of comparing, by the at least one processor, the first scan overhang to the calibration overhang.

The method 900 can further include a step 960 of determining, by the at least one processor, a first level of uncertainty for the CT scanner based on the comparing. In some embodiments, determining the first level of uncertainty can include determining a difference between the first calibration dimension and the first scan dimension. In some embodiments, determining the first level of uncertainty can also include determining a difference between the second calibration dimension and the second scan dimension. In some embodiments, the first level of uncertainty can be used to define a level of precision of the CT scanner.

In some embodiments, the method CT can further include a step of determining, by the at least one processor, a second level of uncertainty for the CT scanner. In some embodiments, determining the second level of uncertainty can include performing iterative optimization, by the at least one processor. The iterative optimization can include iterating the first scan edge, the second scan edge, and/or the floating point, based on the first level of uncertainty. In some embodiments, determining the second level of uncertainty can further include determining a third scan dimension and a fourth scan dimension based on the iterated first scan edge, second scan edge, and/or floating point. In some embodiments, determining the second level of uncertainty can further include determining, by the at least one processor, a second scan overhang based on a difference between the third scan dimension and the fourth scan dimension. In some embodiments, determining the second level of uncertainty can further include comparing, by the at least one processor, the second scan overhang to the calibration overhang. In some embodiments, the iterative optimization can be continued until the level of uncertainty is minimized.

In some embodiments, the method can include using a plurality of CT slice images from the volumetric data of the scan to determine the scan overhang for the apparatus. By considering the plurality of CT slice images to determine the scan overhang for the apparatus, an uncertainty vector can be generated. In some embodiments, the iterative optimization can be continued until the magnitude of the uncertainty vector is minimized. The determining of the levels of uncertainty is described in greater detail below in regard to FIG. 10.

Figure 10:
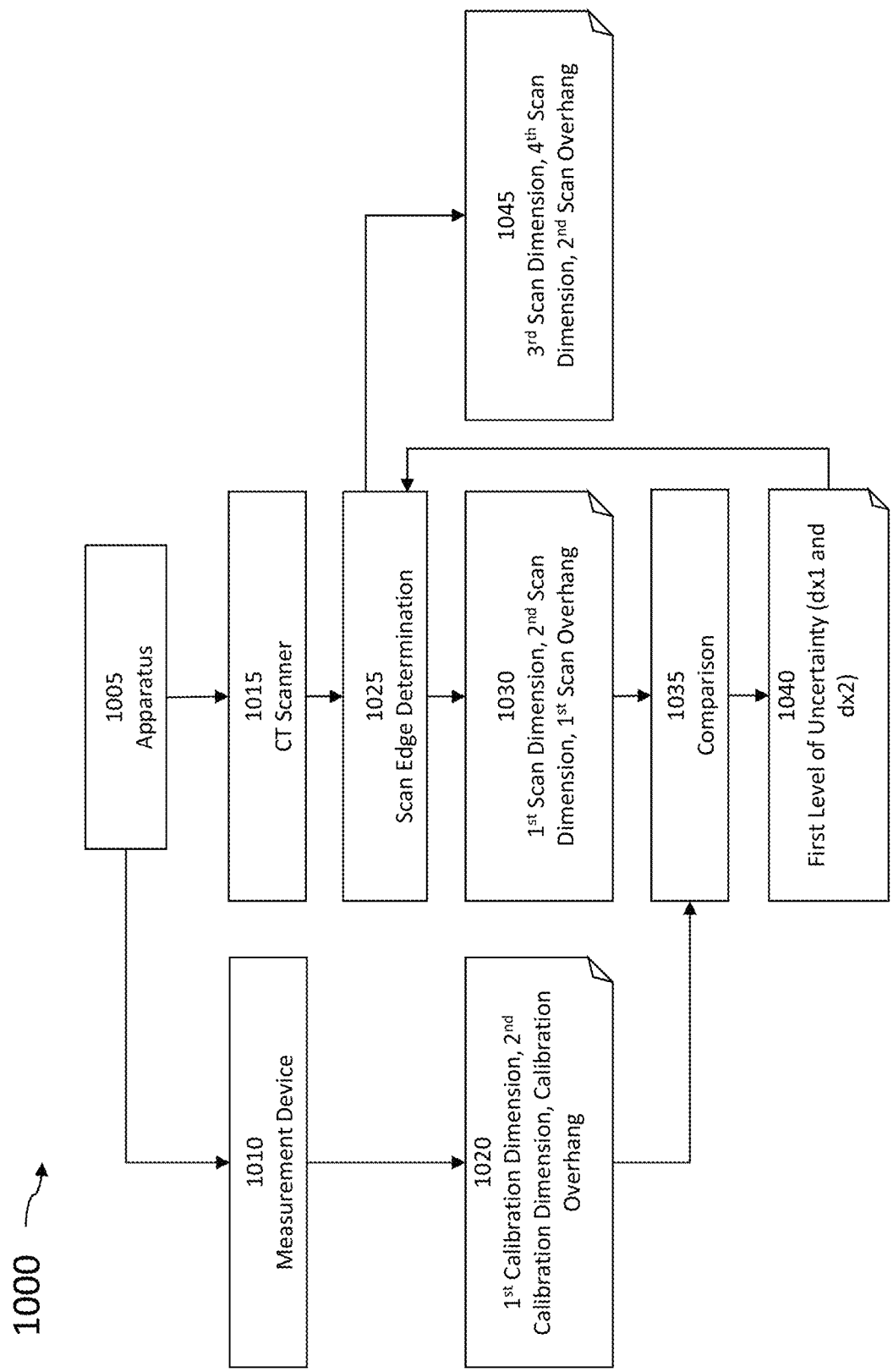
FIG. 10 is a flow diagram illustrating an optimization process of a system for calibrating a CT scanner according to some implementations of the current subject matter.

FIG. 10 is a flow diagram illustrating an optimization process 1000 of a system for calibrating a CT scanner according to an embodiment described herein. In some embodiments, the optimization process 1000 can include using a measurement device 1010 to accurately measure an apparatus 1005 to get a $1^{st}$ Calibration Dimension, $2^{nd}$ Calibration Dimension, and Calibration Overhang 1020. In some embodiments, the measurement device 1010 can be an optical or tactile measurement device or the like. The optimization process can also include scanning the apparatus 1005 by a CT scanner 1015. In some embodiments, the CT scanner 1015 can include at least one processor configured to perform a scan edge determination 1025 to get a $1^{st}$ Scan Dimension, $2^{nd}$ Scan Dimension, and $1^{st}$ Scan Overhang 1030. The optimization process 1000 can also include a comparison step 1035. At the comparison step 1035, the at least one processor of the CT scanner 1015 can be configured to determine a first level of uncertainty 1040. In some embodiments, the first level of uncertainty 1040 can include a first scan dimension uncertainty dx1 and a second scan dimension uncertainty dx2. In some embodiments, dx1 can be determined as a difference between the first scan dimension and the first calibration dimension, and dx2 can be determined as a difference between the second scan dimension and the second calibration dimension. In some embodiments, dx1 and dx2 can be used to optimize the calibration. For example, in the event where dx1 is large, the processor can be configured to move the $1^{st}$ scan dimension determined in order to minimize dx1. A similar process can occur for dx2. The processor can further be configured to determine a $3^{rd}$ Scan Dimension, $4^{th}$ Scan Dimension, and $2^{nd}$ Scan Overhang 1045, where the $3^{rd}$ scan dimension is an optimized $1^{st}$ scan dimension, the $4^{th}$ scan dimension is an optimized $2^{nd}$ scan dimension, and the $2^{nd}$ scan overhang is an optimized $1^{st}$ scan overhang.

In some embodiments, the apparatus 1005 can include a plurality of calibration pairs disposed at multiple locations within the apparatus 1005. In this embodiment, the $1^{st}$ Scan Dimension, $2^{nd}$ Scan Dimension, and $1^{st}$ Scan Overhang 1030 can each be vectors, and the first level of uncertainty 1040 resulting from the comparison 1035 can include uncertainty vectors dx1 and dx2. In this embodiment, the optimization process 1000 can be configured to minimize the magnitude of the uncertainty vectors dx1 and dx2 respectively.

In some embodiments, the optimization process 1000 can be used to optimize the calibration of the CT scanner 1015 so that the difference between the calibration dimensions 1020 determined by the measuring device 1010 and the scan dimensions 1045 (and/or 1025) determined by the CT scanner 1015 are minimized. Secondary to the optimizing the calibration of the CT scanner 1015, the optimization process 1000 can be used to optimize the tip detection capabilities of the CT scanner 1015 that occurs at the scan edge determination 1025 for future scans.

Certain exemplary embodiments have been described to provide an overall understanding of the principles of the structure, function, manufacture, and use of the systems, devices, and methods disclosed herein. One or more examples of these embodiments have been illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

The subject matter described herein can be implemented in analog electronic circuitry, digital electronic circuitry, and/or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another.

Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, can be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language can correspond to the precision of an instrument for measuring the value. Here and throughout the specification and claims, range limitations can be combined and/or interchanged, such ranges are identified and include all the sub-ranges contained therein unless context or language indicates otherwise.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "approximately" includes within 1, 2, 3, or 4 standard deviations. In certain embodiments, the term "about" or "approximately" means within 50%, 20%, 15%, %, 9%, 8%, 7%, 6%, 5%, 4%, 3%, 2%, 1%, 0.5%, or 0.05% of a given value or range. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

One skilled in the art will appreciate further features and advantages of the invention based on the above-described embodiments. Accordingly, the present application is not to be limited by what has been particularly shown and described, except as indicated by the appended claims. All publications and references cited herein are expressly incorporated by reference in their entirety.

The invention claimed is:

1. An apparatus comprising:
   a plurality of body layers configured to extend in a longitudinal direction of the apparatus;
   at least one calibration pair configured to extend in the longitudinal direction of the apparatus and form an interleaved arrangement with the plurality of body layers, the at least one calibration pair comprising
      a first calibration layer having a first edge;
      a second calibration layer having a second edge; and
      one or more opening extending through the first calibration layer and the second calibration layer;
   wherein a first calibration dimension is defined by a distance between the first edge and a first predetermined point within the one or more openings; and
   wherein a second calibration dimension is defined by a distance between the second edge and a second predetermined point within the one or more openings.

2. The apparatus of claim 1, wherein a calibration overhang dimension is defined by a difference between the first calibration dimension and the second calibration dimension.

3. The apparatus of claim 2, wherein the first calibration layer of the calibration pair is an anode layer made from a first material, and second calibration layer of the calibration pair is a cathode layer made from a second material, and the plurality of body layers further comprise:
   a body anode layer made from the first material; and
   a body cathode layer made from the second material, wherein the body anode layer and the body cathode layer form an interleaved arrangement, and the plurality of body layers, the anode layer and the cathode layer are laminated within a battery housing to form a stacked pouch cell.

4. The apparatus of claim 1, wherein the first calibration layer of the calibration pair is an anode layer made from a first material, and second calibration layer of the calibration pair is a cathode layer made from a second material, further wherein the anode layer and the cathode layer are arranged in concentric layers in the longitudinal direction within a battery housing to form a cylindrical cell or a prismatic cell.

5. The apparatus of claim 1, wherein the one or more openings are circular, triangular, square, rectangular, pentagonal, or hexagonal in shape.

6. The apparatus of claim 1, wherein the at least one calibration pair further comprises:
   a first calibration layer support structure having a first end and a second end, the first calibration layer support structure coupled to the first edge of the first calibration layer at the first end and coupled to the second end via at least one clamping mechanism;
   a second calibration layer support structure coupled to the second edge of the second calibration layer at the first end and coupled to the second end via the at least one clamping mechanism; and
   the at least one clamping mechanism coupled to the second end of the first calibration layer support structure and the second end of the second calibration layer support structure to prevent bending of the at least one calibration pair.

7. The apparatus of claim 6, wherein the first calibration layer support structure is formed integrally with the first calibration layer, and the second calibration layer support structure is formed integrally with the second calibration layer.

8. A method comprising:
   scanning, by a CT scanner, an apparatus including a plurality of body layers configured to extend in a longitudinal direction of the apparatus, at least one calibration pair configured to extend in the longitudinal direction of the apparatus and form an interleaved arrangement with the plurality of body layers, the at least one calibration pair comprising a first calibration layer having a first edge, a second calibration layer having a second edge, and one or more openings extending through the first calibration layer and/or the second calibration layer, wherein a first calibration dimension is defined by a distance between the first edge and a first predetermined point within the one or more openings, a second calibration dimension is defined by a distance between the second edge and a second predetermined point within the one or more openings and a calibration overhang measured as a difference between the first calibration dimension and the second calibration dimension;

determining, by at least one processor of a computing system, a first scan edge of the first calibration layer, a second scan edge of the second calibration layer, and one or more floating points within the one or more openings from the scan;

determining, by the at least one processor, a first scan dimension based on a distance between the first scan edge and the one or more floating points;

determining, by the at least one processor, a second scan dimension based on a distance between the second scan edge and the one or more floating points;

determining, by the at least one processor, a first scan overhang based on a difference between the first scan dimension and the second scan dimension;

comparing, by the at least one processor, the first scan overhang to the calibration overhang; and determining, by the at least one processor, a first level of uncertainty for the CT scanner based on the comparing.

9. The method of claim 8, further comprising:
determining, by the at least one processor, a third scan dimension based on the first scan dimension and the first level of uncertainty;
determining, by the at least one processor, a fourth scan dimension based on the second scan dimension and the first level of uncertainty;
determining, by the at least one processor, a second scan overhang based on a difference between the third scan dimension and the fourth scan dimension;
comparing, by the at least one processor, the second scan overhang to the calibration overhang; and
determining, by the at least one processor, a second level of uncertainty for the CT scanner.

10. The method of claim 8, wherein the at least one calibration pair includes a plurality of calibration pairs and the first level of uncertainty includes a first scan dimension uncertainty vector dx1 calculated as a difference between the plurality of first scan dimensions and the plurality of first calibration dimensions, and a second scan dimension uncertainty vector dx2 calculated as a difference between the plurality of second scan dimensions and the plurality of second calibration dimensions.

11. The method of claim 8, wherein the first calibration layer of the calibration pair is an anode layer made from a first material, and second calibration layer of the calibration pair is a cathode layer made from a second material, and the plurality of body layers further include a body anode layer made from the first material, and a body cathode layer made from the second material, wherein the body anode layer and the body cathode layer form an interleaved arrangement, and the plurality of body layers, the anode layer and the cathode layer are laminated within a battery housing to form a stacked pouch cell.

12. The method of claim 8, wherein the first calibration layer of the calibration pair is an anode layer made from a first material, and second calibration layer of the calibration pair is a cathode layer made from a second material, further wherein the anode layer and the cathode layer are arranged in concentric layers in the longitudinal direction within a battery housing to form a cylindrical cell or a prismatic cell.

13. A system comprising:
an apparatus comprising
a plurality of body layers configured to extend in a longitudinal direction of the apparatus;
at least one calibration pair configured to extend in the longitudinal direction of the apparatus and form an interleaved arrangement with the plurality of body layers, the at least one calibration pair comprising
a first calibration layer having a first edge;
a second calibration layer having a second edge; and
one or more openings extending through the first calibration layer and the second calibration layer, wherein; a first calibration dimension is defined by a distance between the first edge and a first predetermined point within the one or more openings, a second calibration dimension is defined by a distance between the second edge and a second predetermined point within the one or more openings, and a calibration overhang measured as a difference between the first calibration dimension and the second calibration dimension; and
a computing system communicatively coupled to a CT scanner, the computing system including at least one processor configured execute the steps of:
scanning the apparatus;
determining a first scan edge of the first calibration layer, a second scan edge of the second calibration layer, and one or more floating points within the one or more openings;
determining a first scan dimension based on a distance between the first scan edge and the one or more floating points;
determining a second scan dimension based on a distance between the second scan edge and the one or more floating points;
determining a first scan overhang based on a difference between the first scan dimension and the second scan dimension;
comparing the first scan overhang to the calibration overhang; and
determining a first level of uncertainty for the CT scanner based on the comparing.

14. The system of claim 13, wherein the first level of uncertainty includes a first scan dimension uncertainty dx1 calculated as a difference between the first scan dimension and the first calibration dimension, and a second scan dimension uncertainty dx2 calculated as a difference between the second scan dimension and the second calibration dimension.

15. The system of claim 13, further comprising:
a measuring device configured to measure the first calibration dimension and the second calibration dimension.

16. The system of claim 13, wherein the first calibration layer of the calibration pair is an anode layer made from a first material, and second calibration layer of the calibration pair is a cathode layer made from a second material, and the plurality of body layers further comprise:

a body anode layer made from the first material; and a body cathode layer made from the second material, wherein the body anode layer and the body cathode layer form an interleaved arrangement, and the plurality of body layers, the anode layer and the cathode layer are laminated within a battery housing to form a stacked pouch cell.

17. The system of claim 13, wherein the first calibration layer of the calibration pair is an anode layer made from a first material, and second calibration layer of the calibration pair is a cathode layer made from a second material, further wherein the anode layer and the cathode layer are rolled in the longitudinal direction and placed within a battery housing to form a cylindrical cell or a prismatic cell.

18. The system of claim 13, wherein the at least one calibration pair further comprises:

a first calibration layer support structure configured to couple at a first end to the first edge of the first calibration layer and configured to couple at a second end to at least one clamping mechanism;

a second calibration layer support structure configured to couple at a first end to the second edge of the second calibration layer and configured to couple at a second end to the at least one clamping mechanism; and the at least one clamping mechanism configured to clamp the second end of the first calibration layer support structure and the second end of the second calibration layer support structure to prevent bending of the at least one calibration pair.

19. The system of claim 18, wherein the first calibration layer support structure is formed integrally with the first calibration layer, and the second calibration layer support structure is formed integrally with the second calibration layer.

20. The apparatus of claim 1, wherein the one or more openings include a single opening extending through the first calibration layer and the second calibration layer and the first predetermined point is coincident with the second predetermined point.

\* \* \* \* \*